(12) United States Patent
 Kang

(10) Patent No.: US 9,131,970 B2
(45) Date of Patent: Sep. 15, 2015

(54) PIN ASSEMBLY FOR OPERATION CAPABLE OF INTRODUCING DRUG

(71) Applicant: National Cancer Center, Goyang-si (KR)

(72) Inventor: Hyun Guy Kang, Goyang-si (KR)

(73) Assignee: National Cancer Center (KR)

( * ) Notice: Subject to any disclaimer, the term of this patent is extended or adjusted under 35 U.S.C. 154(b) by 191 days.

(21) Appl. No.: 13/915,377

(22) Filed: Jun. 11, 2013

(65) Prior Publication Data

US 2013/0345763 A1  Dec. 26, 2013

Related U.S. Application Data

(63) Continuation-in-part of application No. 12/190,822, filed on Aug. 13, 2008, now abandoned.

(30) Foreign Application Priority Data

Jun. 23, 2008  (KR) ........................ 10-2008-0059222

(51) Int. Cl.
| | |
|---|---|
| A61B 17/84 | (2006.01) |
| A61B 17/70 | (2006.01) |
| A61B 17/86 | (2006.01) |
| A61B 17/34 | (2006.01) |
| A61M 5/158 | (2006.01) |
| A61M 5/32 | (2006.01) |
| A61F 2/46 | (2006.01) |
| A61B 17/74 | (2006.01) |
| A61M 25/00 | (2006.01) |

(52) U.S. Cl.
CPC ........... *A61B 17/846* (2013.01); *A61B 17/3472* (2013.01); *A61B 17/7098* (2013.01); *A61B 17/864* (2013.01); *A61M 5/158* (2013.01); *A61M 5/32* (2013.01); *A61B 17/744* (2013.01); *A61F 2/4601* (2013.01); *A61M 25/007* (2013.01)

(58) Field of Classification Search
CPC ............. A61B 17/846; A61B 17/7098; A61B 17/864; A61B 17/3472
USPC ................................ 606/65, 104, 100, 92–94
See application file for complete search history.

(56) References Cited

U.S. PATENT DOCUMENTS

| | | | |
|---|---|---|---|
| 6,048,343 A * | 4/2000 | Mathis et al. ................. 606/916 |
| 6,210,376 B1 | 4/2001 | Grayson | |
| 7,699,852 B2 | 4/2010 | Frankel et al. | |
| 2004/0002713 A1 | 1/2004 | Olson et al. | |
| 2004/0122431 A1 | 6/2004 | Biedermann et al. | |
| 2005/0107800 A1 | 5/2005 | Frankel et al. | |

FOREIGN PATENT DOCUMENTS

| | | |
|---|---|---|
| FR | 2820630 | 8/2002 |
| KR | 10-2003-0037616 | 5/2003 |

(Continued)

*Primary Examiner* — Andrew Yang
(74) *Attorney, Agent, or Firm* — Casimir Jones SC

(57) ABSTRACT

A pin assembly for operation includes a hollow pin for operation having a plurality of side holes defined through an outer surface thereof and a head which is closed or open due to the presence of a through-hole; a hollow support having a pin fastening part formed therein in the shape of a groove to fasten one end of the pin for operation, and being open at both ends thereof, and a hollow injector for insertion into an insertion hole formed in the support, wherein the hollow pin for operation is fastened to the pin fastening part of the support, and by applying external force to one end of the support, the hollow pin for operation is inserted into a bone.

15 Claims, 13 Drawing Sheets

(56) References Cited

FOREIGN PATENT DOCUMENTS

| KR | 10-2004-0031590 | | 4/2004 |
|---|---|---|---|
| WO | 00/54705 | A1 | 9/2000 |
| WO | 2004098421 | | 11/2004 |
| WO | 2005/053545 | A2 | 6/2005 |
| WO | 2006/011152 | | 2/2006 |
| WO | 2006090226 | | 8/2006 |
| WO | 2007/122608 | A2 | 11/2007 |

* cited by examiner

A

B

C

D

E

F

G

H

I

J

A

B

C

D

A

B

PIN ASSEMBLY FOR OPERATION CAPABLE OF INTRODUCING DRUG

This application is a continuation-in-part of U.S. patent application Ser. No. 12/190,822, filed Aug. 13, 2008, which claims priority to Korean Patent Application No. 10-2008-0059222, filed Jun. 23, 2008, each of which are herein incorporated by reference in its entirety.

TECHNICAL FIELD

The present invention relates to a pin assembly for operation and, more particularly, to a bendable pin assembly for operation in which a plurality of holes are defined through the wall and the head thereof, thus facilitating introduction of various medication and treatment agent therethrough.

BACKGROUND ART

These days, despite the development of diagnosis and treatment techniques for cancer patients, the number of patients who suffer pain due to spreading of cancer to the bone increases. In America alone, 1.2 millions of people are newly diagnosed with cancer every year, and 50% of these develop bone metastases according to statistics. Most cancers tend to spread to the bone, and approximately 20 to 80% of bone metastases have been reported according to the types of the cancers.

The cancer cells spreading to the bone cause bone melting and weakening, thus cause pathologic fracture or impending fracture, which is accompanied with severe pain and serious functional disabilities. Most bone metastases have multiple occurrences. Although advanced cancer patients are in need of surgical operation, it certainly is the great burden as well as high risk to both the patient and the medical professionals, as the surgical procedure involves incision of skin and muscles of the patient who already has unstable general condition or in need of on-going chemotherapy.

While the aged people take up large portion of the cancer patient population, the aged patients are more likely to develop osteoporotic bone fractures due to occurrence of osteoporosis generated in the process of cancer treatment. Such condition has high risk of developing into complications such as non-union of the fracture sites, weakness of general condition or loss of limb functions.

Therefore, efforts are necessary, to provide a surgical treatment of the involved bone that can be conducted in a simple and efficient manner, while preserving the general condition as much as possible, and without causing complications, particularly for the senile patients or advanced cancer patients.

The main treatment generally involves invasive surgery which includes incising skin and muscles to form bony window on the bone, curettage of tumor mass, reinforcing with bone cement, and using intramedullary nail or plate, tumor prosthesis or joint replacement arthroplasty.

A method for facilitating bone-union to treat the osteoporotic bone fracture generally involves fixing the fracture site with intramedullary nail or plate, defining a hole in the bone, inserting an injector, and introducing osteoinductive or osteoconductive bone substitutes therethrough. Materials for direct coating to promote bony incorporation on the stem of prosthesis and to prevent bone resorption have been used. In other words, the implant is required to play a role of drug-deliverer, as well as bone fixer.

Although percutaneous bone cement injection is used for the osteoporotic spinal compression fracture or metastatic bone cancer, it is difficult to prevent pathologic fracture particularly at the long bone of limb, in the absence of the internal fixation of metal implant. However, when the bone metastasis is accompanied with osteoporosis or progressed bone fracture, the internal metal fixator easily loosens out of the bone due to weakened bone, which is problematic. Accordingly, improved bone fixation method is necessary, which plays a role of not only the internal metal fixator, but also treatment agent injector.

Accordingly, an effective bone augmentation and stabilization surgical method is necessary, which can minimize surgical risks of the patients which may already have deteriorated general condition and also effectively reinforce weakening bones.

DISCLOSURE

Technical Problem

Accordingly, the present invention has been made keeping in mind the above problems occurring in the related art, and an object of the present invention is to provide a pin assembly for operation which can solve the problems caused due to extensive surgery and allow medication or treatment agent to be easily injected to a treatment position, wherein, a pin for operation is inserted into the bone percutaneously and without requiring incision of skin or muscle, and various medications are injected through the pin in fixed position to reinforce the strength of the bone and to suppress the progress of the bone metastasis.

Technical Solution

In order to achieve the above objects, according to one aspect of the present invention, there is provided a pin assembly for operation, comprising a hollow pin for operation having a plurality of side holes defined through an outer surface thereof and a head which is closed or open due to the presence of a through-hole; a hollow support having a pin fastening part formed therein in the shape of a groove to fasten one end of the pin for operation, and being open at both ends thereof, and a hollow injector for insertion into an insertion hole formed in the support, wherein the hollow pin for operation is fastened to the pin fastening part of the support, and by applying external force to one end of the support, the hollow pin for operation is inserted into a bone curvature.

According to another aspect of the invention, the hollow pin for operation comprises the plurality of side holes defined through the outer surface thereof and a thread defined on the head.

According to another aspect of the invention, the hollow pin for operation comprises a hollow conduit connected with one end to the head, and a cover for screw-coupling with the head to define a predetermined space corresponding to a predetermined distance from an outer circumference of the conduit, and comprising a plurality of side holes defined therein, wherein an externally-injected material is stored in the predetermined space.

According to another aspect of the invention, the pin assembly for operation may additionally include a hollow driver comprising a through-hole formed therein, the hollow driver for insertion into an opening at one side of the hollow pin for operation.

According to another aspect of the invention, the head of the hollow pin for operation is sharp, blunt or bent to one side.

According to another aspect of the invention, the hollow pin for operation comprises side holes defined at an end of the head.

According to another aspect of the invention, the hollow pin for operation comprise a fastening part at an end of the body.

According to another aspect of the invention, the fastening part removably fastens the hollow pin for operation to the support by screw coupling.

According to another aspect of the invention, the pin assembly for operation may additionally include a stylet for insertion into the injector.

According to another aspect of the invention, the injector comprises a handle with which it is possible to adjust a leading end of the injector to be positioned at the side holes of the hollow pin for operation in need of medication injection.

According to another aspect of the invention, the pin assembly for operation may additionally include a T-shaped impactor for insertion in between the insertion hole on the inner side of the support and the injector, the T-shaped impactor comprising a through-hole defined along the center.

According to another aspect of the invention, a guide pin or a reinforcement metal wire is inserted into the through-hole of the head of the hollow pin for operation.

According to another aspect of the invention, the hollow pin for operation is formed from stainless steel, titanium or an alloy using the same.

According to still another aspect of the present invention, medication or bone cement is injected through the holes defined in the pin for operation into the bone.

According to still a further aspect of the present invention, the medication is selected from the group consisting of alcohol, liquid nitrogen, anticancer medicine, bone regenerating material, and anti-resorptive agent.

According to various embodiments, the pin assembly for operation does not require rather wide skin or muscle incision as is required by the conventional examples, but only defines a hole on the skin, while it provides medication to suppress tumor cells or bone resorption cell such as osteoclast, or bone cement through the conduit and holes of the pin for operation to thus reinforce weakened or fractured bone part and fix the pin for operation in position in the bone. That is, it is possible to percutaneously fix the weakened bone using pin for operation, while injecting various medications and treatment agents through the pin for operation inserted in the bone, without having to separately define a hole in the bone.

BRIEF DESCRIPTION OF DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
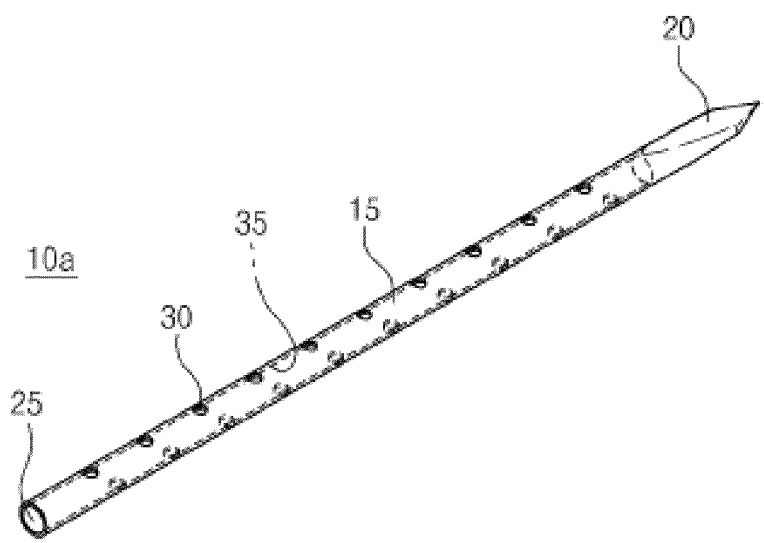
FIGS. 1a through 1j are schematic perspective views illustrating various configurations of a pin which is used in a pin assembly for operation according to the present invention.
Figure 1:
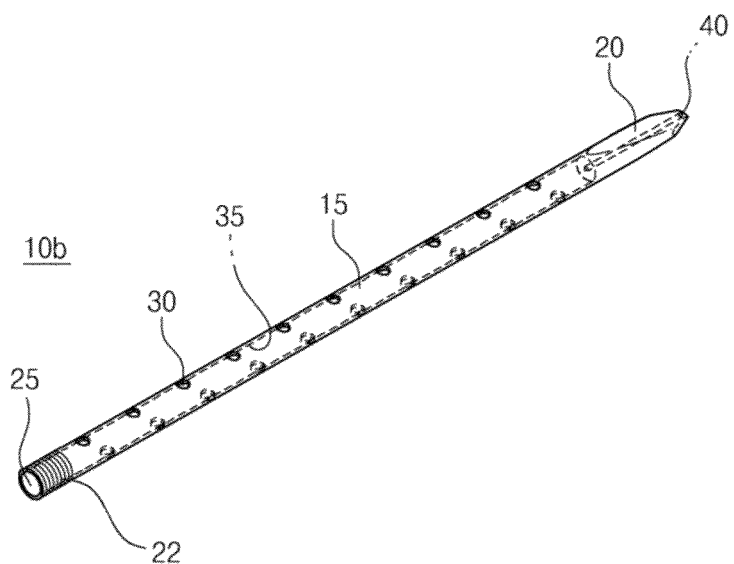
Figure 1:
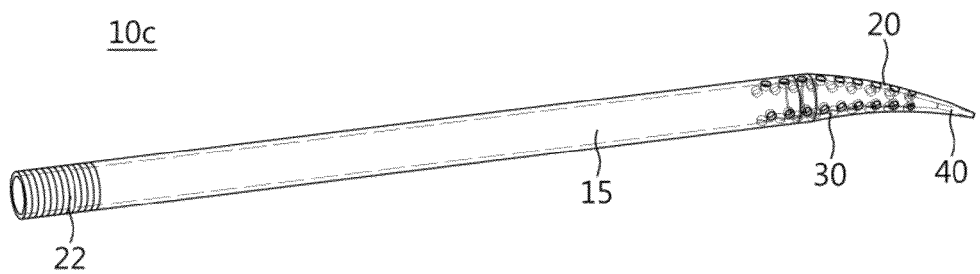
Figure 1:
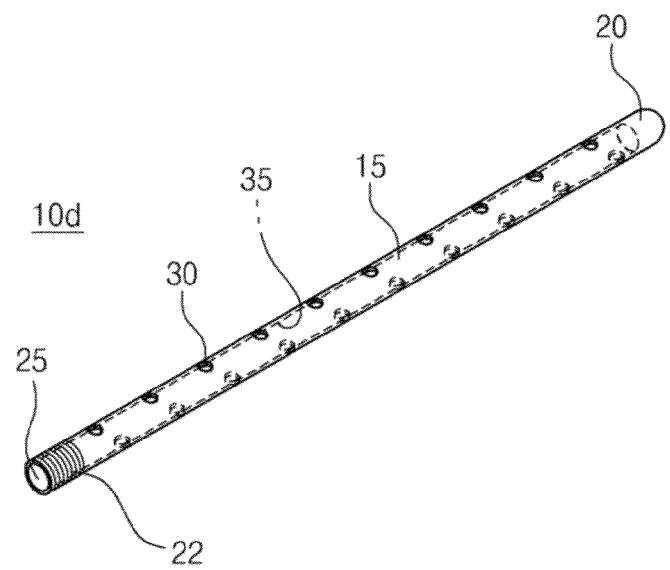
Figure 1:
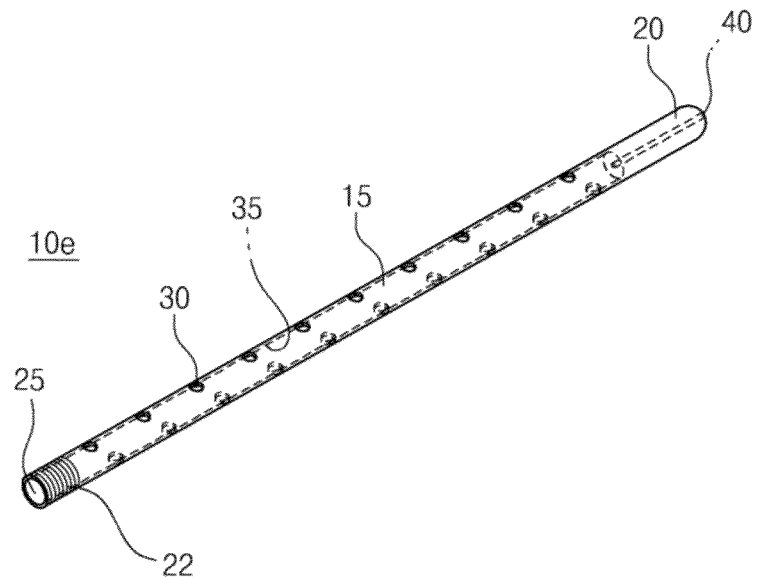
Figure 1:
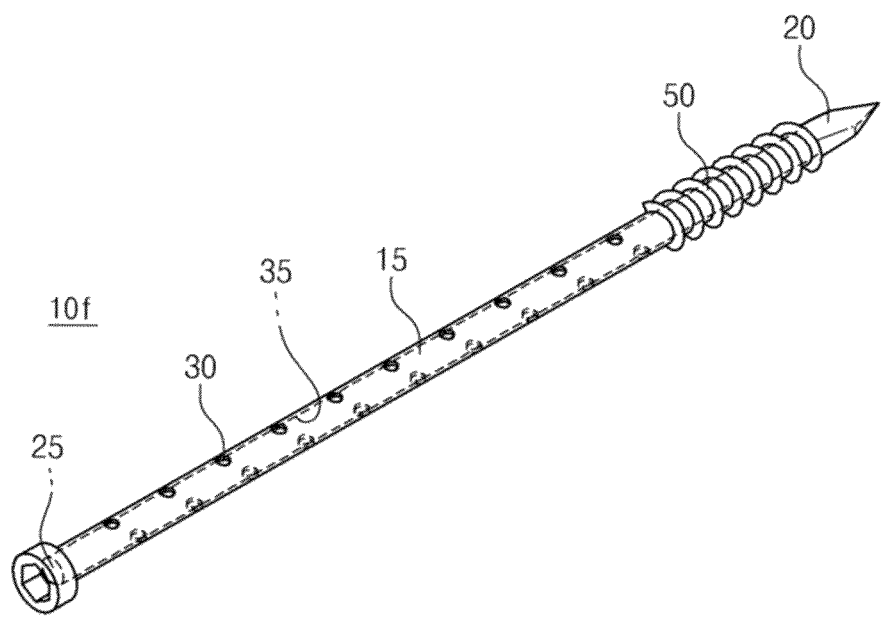
Figure 1:
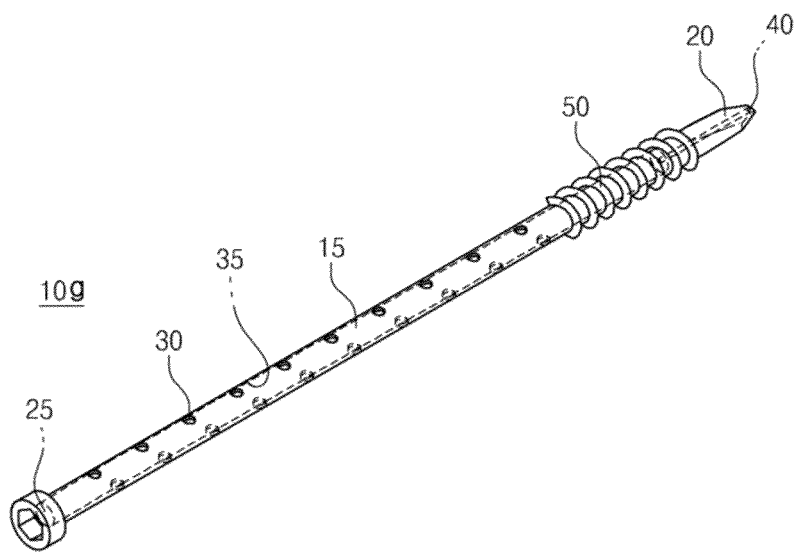
Figure 1:
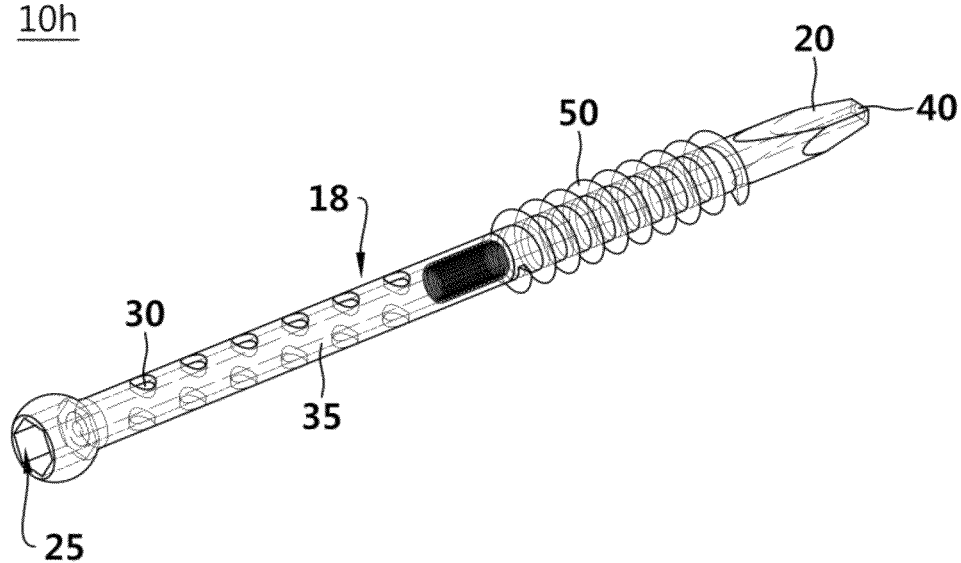
Figure 1:
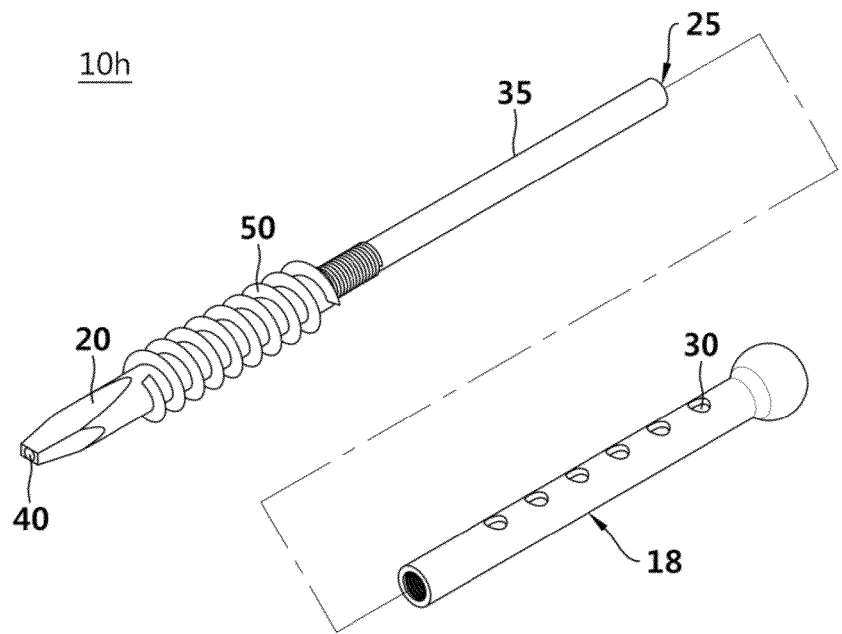
Figure 1:
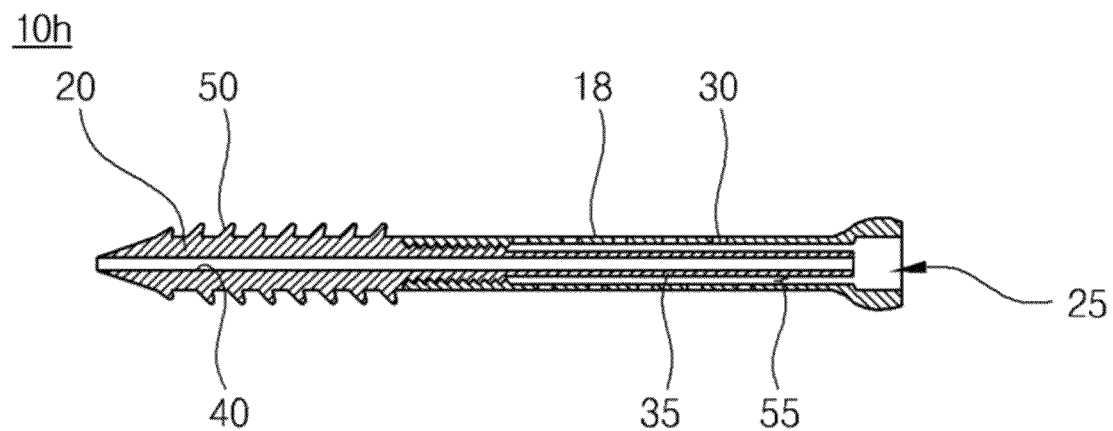

Reference will now be made in greater detail to preferred embodiments of the invention, examples of which are illustrated in the accompanying drawings. Wherever possible, the same reference numerals will be used throughout the drawings and the description to refer to the same or like parts.

FIGS. 1a through 1j are schematic perspective views illustrating various configurations of a pin which is used in a pin assembly for operation according to the present invention.

Referring to FIGS. 1a through 1j, each of pins 10 for operation, which are used in the present invention, has a configuration of a hollow elongate bar which has a plurality of side holes 30 defined through the outer wall thereof. Each pin 10 for operation has a straight body 15 which has the side holes 30 defined through the wall thereof and a head 20 which is formed on the distal end of the body 15 and is brought into contact with the bone or another portion of the human body.

Depending on embodiments, the pins for operation may be classed into two types. For example, FIGS. 1a to 1e illustrate nail-type pin, while FIGS. 1f to 1j illustrate screw-type pin.

Referring to FIGS. 1a to 1e, the nail type pin for operation may have a sharp or blunt head 20, and a fastener 22 formed at an end of the straight body 15 for screw-coupling with the support for pressing the pin. To be specific, FIG. 1a illustrates a pin 10a for surgical operation, having a sharp head 20 and the fastener 22 at an end of the straight body 15 for surgical operation, and a closed end of the head 20. FIG. 1b illustrates a pin 10b for surgical operation similar to that illustrated in FIG. 1a, but different in terms of the presence of a through-hole 40 extended from an open end of the head 20. FIG. 1c illustrates a pin 10c for surgical operation, in which the head 20 has a bent end for easy insertion into the long bone of limb, and a side hole 30 formed only on an end of the head 20. The pin 10c for surgical operation is bendable to conform to the curves of the bone. The pin 10c for surgical operation may be bent within an appropriate range using tools such as press bender or the like as equipped in the operation room.

FIGS. 1d and 1e illustrate pins 10d, 10e for surgical operation, provided in the form of intramedullar nail having a blunt head 20. Referring to FIG. 1d, the pin 10d for surgical operation has a blunt head 20 with closed end, while referring to FIG. 1e, the pin 10e for surgical operation has a blunt head 20 with an open end where the through-hole 40 is formed.

That is, the nail type pin for surgical operation may have sharp or blunt head 20, with an end thereof being possibly bent partially for easy insertion into a long bone of limb. Further, an end of the head 20 may be open or closed, and the open head 20 may have a through-hole 40 formed therein. When the side hole 30 is formed only in an end of the head 20, it is possible to partially adjust the site of intramedullar drug injection. Further, as explained above, the intramedullar nail may include the fastener 22 formed at an end of the straight body 15 to play a role of a support. The fastener 22 may preferably be $\frac{1}{15}$ to $\frac{1}{10}$ the entire length of the pin for surgical operation.

Meanwhile, referring to FIGS. 1f to 1j, the screw type pin for surgical operation may include a sharp head 20 and a thread 50 formed on the head 20. To be specific, FIG. 1f illustrates a pin 10f for surgical operation with a closed end, which has a sharp head 20 and a thread 50 formed on the sharp head 20, while FIG. 1g illustrates a pin 10g for surgical operation with an open end, which has a sharp head 20, a thread 50 formed on the sharp head 20, and a through-hole 40 formed in the end of the head 20. It is preferable that the thread 50 formed on the screw type pin for surgical operation may be ⅕ to ⅓ the entire length of the pin for surgical operation.

Further, FIGS. 1h to 1j illustrate a screw type pin 10h for surgical operation in different configuration. FIG. 1h is a perspective view of the pin 10h for surgical operation, FIG. 1i is a perspective view illustrating a cover 18 separated from the pin 10g for surgical operation, and FIG. 1j is a sectional view of FIG. 1h. To be specific, the pin 10h for surgical operation as illustrated in FIGS. 1i to 1j may include a hollow conduit 35 connected at one end to the head 20, and a cover 18 screw-coupled with the head 20 to define a predetermined space 55 at a predetermined distance from an outer circumferential surface of the hollow conduit 35, and having a plurality of side holes 30 formed therein, in which an externally-injected substance may be stored in the predetermined space 55. Further, a guide pin (not illustrated) may be provided so that the screw type pin 10h is inserted along the guide pin (not illustrated). Further, after the screw type pin 10h is inserted, drug or treatment agent may be injected without removing the guide pin (not illustrated), to ensure intra-osseous intrusion only through the side holes, i.e., to ensure that the drug or treatment agent does not leak through the end of the head which serves as a passage for the guide pin.

Referring to FIG. 1i, the conduit 35 may have a smaller diameter than that of the thread 50 of the head 20, so as to be inserted into an interior of the cover 18. Due to the above-mentioned structure, externally-introduced substance such as, for example, drug or bone cement can move in the predetermined space 55 in the interior of the conduit 35 and the predetermined space 55 between the conduit 35 and the cover 18. More material such as drug may be stored, as the predetermined space 55 is larger, and the material can be continuously supplied to a site in need of treatment through the side holes 30. Accordingly, drug can be continuously supplied for an extended period of time so that the treatment effect is maximized.

As a surgeon inserts the pin 10 for operation shown in each of FIGS. 1a through 1j into the bone of a patient and injects medication or bone cement through an inlet port 25 which is defined at the proximal end of the pin 10 for operation, the medication or bone cement flows through an internal passage of the pin 10 for operation and is introduced into the bone through the side holes 30 and the through-hole 40.

The injection amount of the medication or bone cement or a treatment position can be adjusted by changing the sizes and the positions of the side holes 30 and the through-hole 40 so that medial treatment can be given in accordance with an order of priority.

The pin 10 for operation can be made of stainless steel and, as a matter of course, may be made of an antirust alloy. For instance, titanium or a titanium-based alloy can be used.

A guide pin 70 or a reinforcing metal wire can be additionally provided in a manner such that it is inserted through the through-hole 40 of the pin 10 for operation to reinforce the strength of the pin 10 for operation. In the same manner as the pin 10 for operation, the guide pin 70 or the reinforcing metal wire can be made of stainless steel or an antirust alloy. It is preferred that titanium or a titanium-based alloy be used.

In the case that the guide pin 70 or the reinforcing metal wire is inserted through the internal passage 35 which is defined in the pin 10 for operation, the guide pin 70 or the reinforcing metal wire can be bent simultaneously with the pin 10 for operation. In this case, the guide pin 70 or the reinforcing metal wire can be bent using a press bender in an allowable range in conformity with a degree to which a bone as the target of operation is curved.

Bone cement can be introduced into the bone through the internal passage 35 which is defined in the pin 10 for operation. The bone cement reinforces the bone, prevents the inserted pin 10 for operation from being released out of the bone, increases the coupling strength between the bone and the pin 10 for operation, and generates heat while being set, so as to cause the death of cancer cells.

The medication capable of being injected through the pin 10 for operation includes 100% alcohol which can cause the death of cancer cells, liquid nitrogen which can quickly freezing cancer cells and cause the death of the cancer cells, anticancer medicine which can be introduced into the bone while being mixed with bone cement, to continuously cause the death of cancer cells, bone regenerating material which can promote bone union in a fractured portion of the bone, and anti-resorptive agent which can prevent osteoporosis and bone destruction from proceeding.

Figure 2:
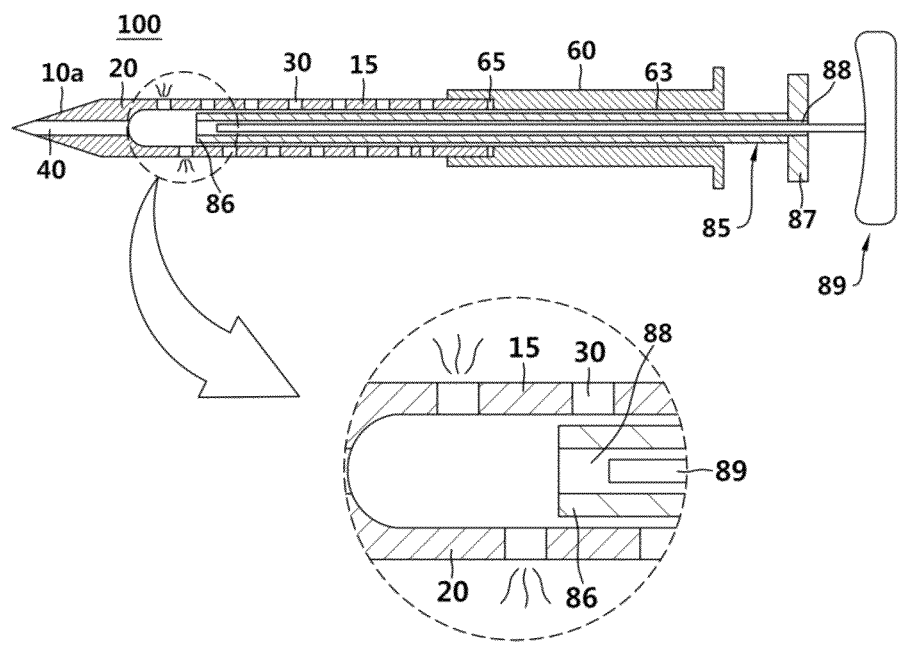
FIGS. 2a through 2d are sectional views illustrating a nail-type pin assembly 100, 100', 100", 100'" for operation in accordance with one embodiment of the present invention.
Figure 2:
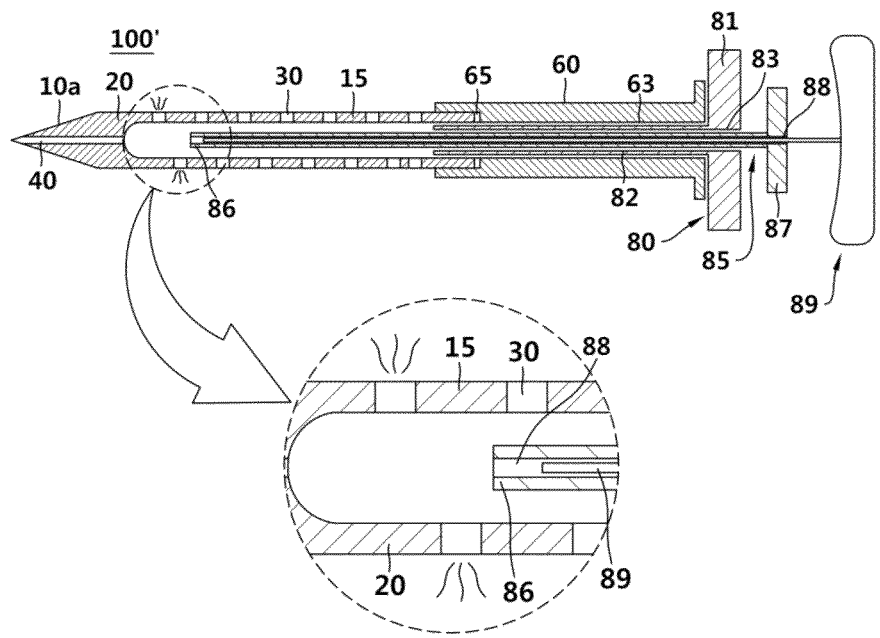
Figure 2:
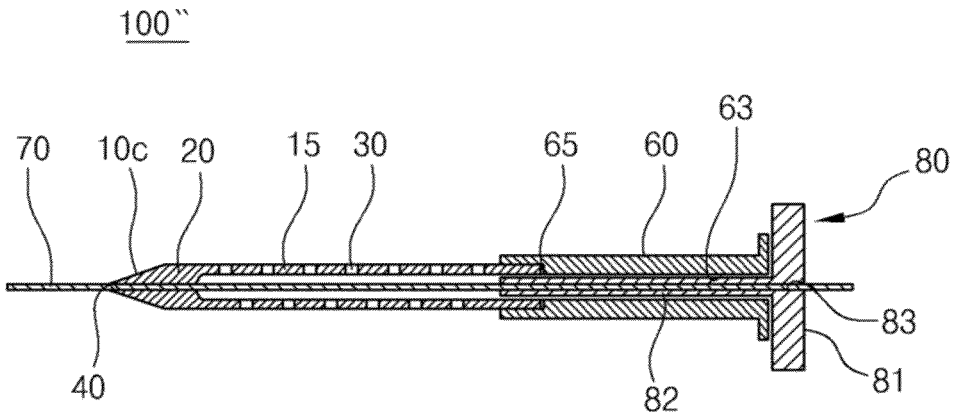
Figure 2:
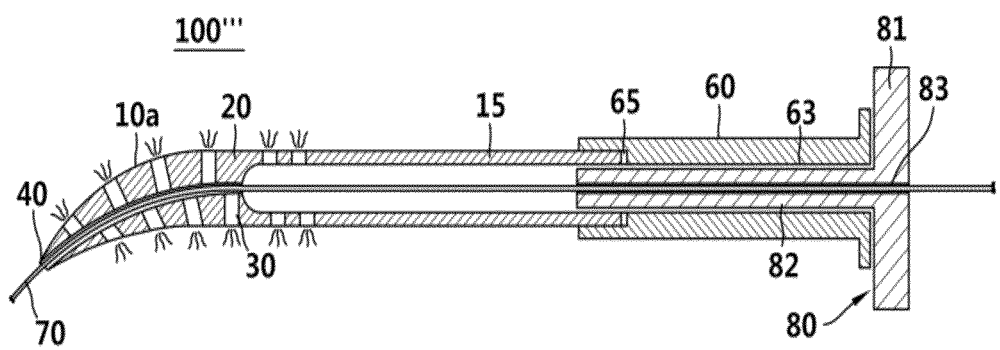

FIG. 2 is a sectional view illustrating a nail type pin assembly 100, 100', 100", 100''' for operation in accordance with one embodiment of the present invention.

In one embodiment, the pin assembly 100 for operation shown in FIG. 2a is composed of a hollow pin 10b for operation which has a plurality of side holes 30 defined through the wall thereof and in which a head 20 is sharply formed and is closed, a hollow support 60 in which a pin fastening part 65 is formed in the shape of a groove to fasten the proximal end of the pin 10 b for operation and both ends of the support 60 are open, a hollow injector 85 insertable into an insertion hole 63 defined through the support 60 and thereof stylet 89 for insertion into a guide part 88 of the injector 85.

To be specific, the hollow injector 85 may be placed into the pin for operation, by being inserted in the insertion hole 63 within the support 60, with a leading end 86 being placed at a location of the side holes 30 of the pin for operation to thus allow intra-osseous intrusion of a medication or treatment agent to an intended site. The medication may be injected using a needle (not illustrated) containing medication or bone cement into the guide part 88 of the hollow injector 85, and the stylet 89 may be used to enable efficient intra-osseous intrusion of the medication or bone cement.

Although the size of the hollow injector 85 is not strictly limited as long as this can be placed at the side holes 30, in one preferred embodiment, the hollow injector 85 may have a similar or longer length than that of the insertion hole 62 of the pin 62 for operation according to an embodiment of the present invention. Further, although the hollow injector 85 may have a width that enables insertion into the insertion hole 63 of the support 60, such is not specifically limited as long as the hollow injector 85 allows movement into the insertion hole 63 and adjustment of injection site of the medication or bone cement.

Depending on embodiment, the pin assembly 100' for operation may include a T-shaped impactor 80 for insertion between the insertion hole 63 and the hollow injector 85 inside the support of the pin assembly 100 for operation, as is illustrated in FIG. 2b.

The pin assembly 100' for operation shown in FIG. 2b is composed of a hollow pin 10b for operation which has a plurality of side holes 30 defined through the wall thereof and in which a head 20 is sharply formed and a through-hole 40 is defined through the head 20, a hollow support 60 in which a pin fastening part 65 is formed in the shape of a groove to fasten the proximal end of the pin 10c for operation and both ends of the support 60 are open, a T-shaped impactor 80 which is inserted into an insertion hole 63 defined through the support 60 and an injector 85 for insertion into a through-hole 83 of the impactor 80.

The impactor 80 may insert the pin 10b for operation into a bone when external force is exerted to a collision part 81 of the impactor 80. The support 60 may be formed to insert the pin for operation into a bone, and the support 60 or the impactor may preferably be formed from a material that does not easily deform or break by the external force.

With the impactor 80 as the one illustrated in FIG. 2b is provided, the support 60 inserts the pin 10b for operation into a bone by the external force exerted to one end thereof, and when the pin 10b for operation is planted within a bone for treatment, the impactor 80 is removed and medication or bone cement is injected through the hollow support 60 or the injector 85 which is open on both ends. The medication or bone cement moves to a site for treatment, and suppresses bone metastasis and bone fracture, and also reinforce the bone as it hardens within the bone.

On the contrary, when no impactor 80 is provided as in the case of FIG. 2a, the support 60 inserts the pin 10b for operation into a bone as external force is exerted onto one end of the support 60. Then after the pin 10a for operation is planted within the bone for treatment, medication or bone cement is injected through the hollow support 60 with both open ends. Since the medication or bone cement moves to a site for treatment within the bone via the side holes 30, it is possible to adjust the location of the site for treatment using the injector 85.

The pin assembly 100' for operation may also include a guide pin 70 or a reinforcing metal wire which is installed by being inserted through the through-hole 83 of the impactor 80 and the through-hole 40 defined through the head 20 of the pin 10b for operation. After the surgeon drives the guide pin 70 through the skin into the bone, by applying external force to the support 60 or the impactor 80, the pin 10b for operation is driven into the bone along the path of the guide pin 70, as shown in FIG. 2c.

The flexible guide pin 70 functions to guide the pin 10b for operation so that the pin 10b for operation can be easily fixed intramedullary, i.e., easily driven into the bone. In this regard, as the occasion demands, by not removing the guide pin 70 but leaving an appropriate length of the guide pin 70, the guide pin 70 can serve to reinforce the strength of the pin 10b for operation in the same way as the reinforcing metal wire.

Hence, after inserting the guide pin 70 into the pin 10b for operation, the guide pin 70 and the pin 10b for operation are simultaneously bent using a press bender, etc., and then, by applying external force to them, they can be driven into the bone.

Meanwhile, a nail type pin for operation may be bent before being driven into the bone, to suit the configuration of the long bone of limb such as femur, humerus, or tibia. The nail type pin for operation may have a plurality of side holes defined on only an end thereof, as is illustrated in FIG. 2d.

To be specific, a pin assembly 100" for operation includes a sharp bent head 20, a hollow pin 10c for operation which has a plurality of side holes 30 defined through an end of the head 20, a hollow support 60 having a pin fixer 65 formed in groove configuration on an inner side to fix an end of one side of the pin 10c for operation and having both open sides, and a T-shaped impactor 80 for insertion into an insertion hole 63 formed on an inner side of the support 60 and having a through-hole 83 defined in the center thereof.

With the pin 10c for operation driven into the bone for treatment, medication or bone cement is injected through the support 60. The medication or bone cement, when injected, moves past an inlet port, the side holes 30 and the through-hole 40 formed on an end of the head 20 and to the site for treatment inside the bone and causes cancer cell death or hardens in the bone.

The pin for operation for use in the pin assembly 100, 100', 100", 100''' may be replaced depending on use. For example, when the thread 50 is formed on the head 20 of the pin for operation, the pin for operation may be rotated along the path of the thread to be driven into the bone, and this can be used particularly when the bone is relatively weak or to fix relatively short bone, as is illustrated in FIG. 3.

Figure 3:
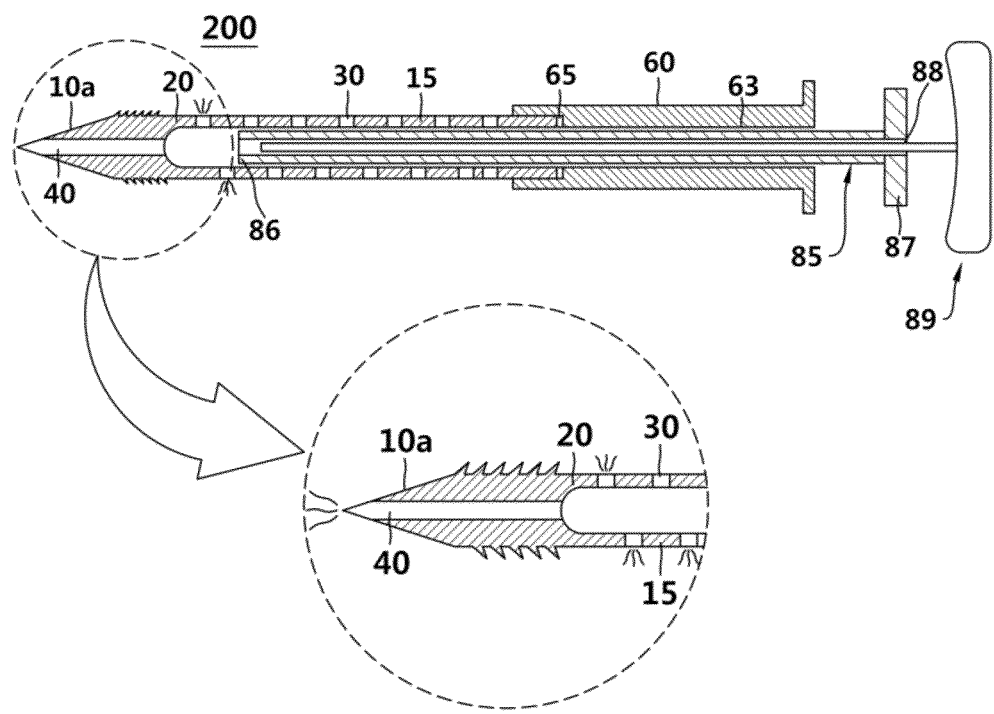
FIG. 3 is a sectional view or perspective view illustrating a screw type pin assembly for operation in accordance with another embodiment of the present invention.

FIG. 3 provides sectional view and perspective view of a pin assembly 200 for operation using screw type pin for operation.

Referring to FIG. 3, a 1 g pin 10g for operation is used in the pin assembly 200 for operation, according to an embodiment of the present invention. To be specific, the screw type pin assembly 200 for operation illustrated in FIG. 3 may include a sharp hollow pin 10g for operation having a plurality of side holes 30 formed on an outer surface, an open head 20 at an end, a through-hole 40, and a thread 50 formed on the head 20, a pin support 65 formed in groove configuration to fix an end of one side of the pin 10g for operation, a hollow support 60 with both open sides, a hollow injector 85 for insertion into an insertion hole 63 defined inside the support 60, and a stylet 89 for insertion into a guide 88 of the injector 85.

Figure 4:
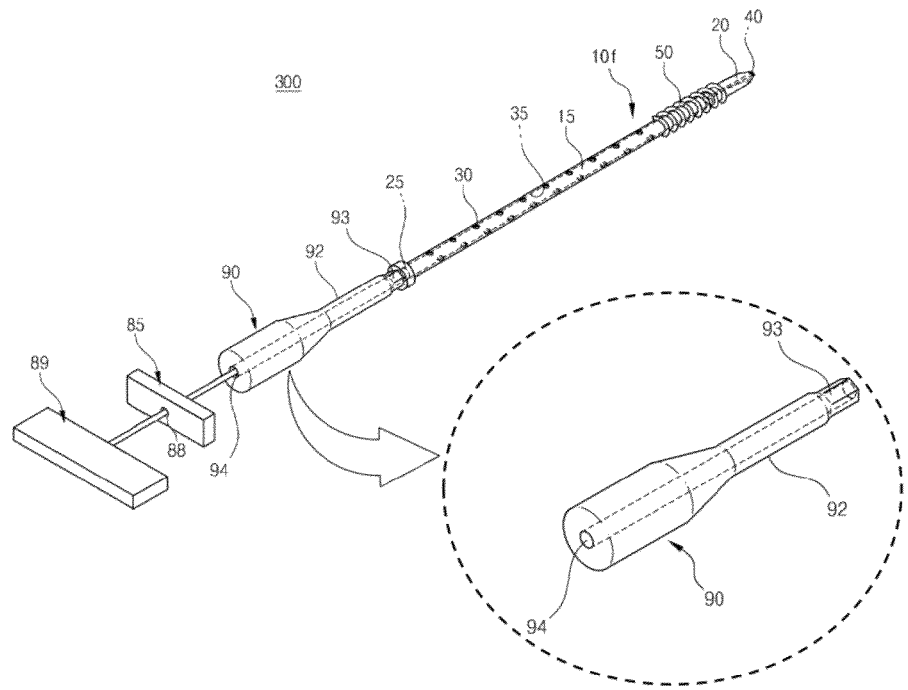
FIGS. 4a through 4b are perspective views illustrating a screw type pin assembly for operation in accordance with yet another embodiment of the present invention.
Figure 4:
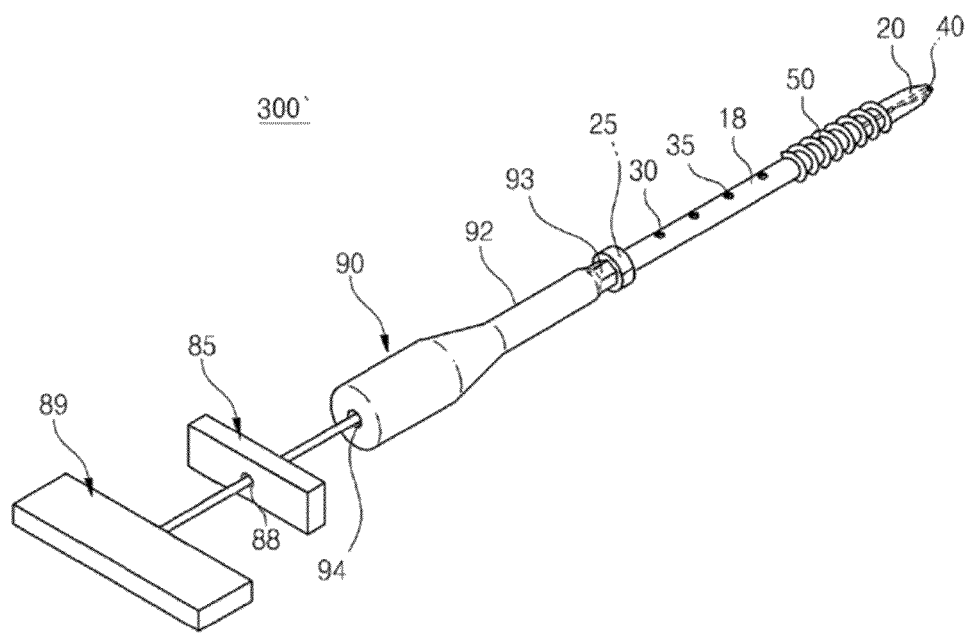
Figure 5:
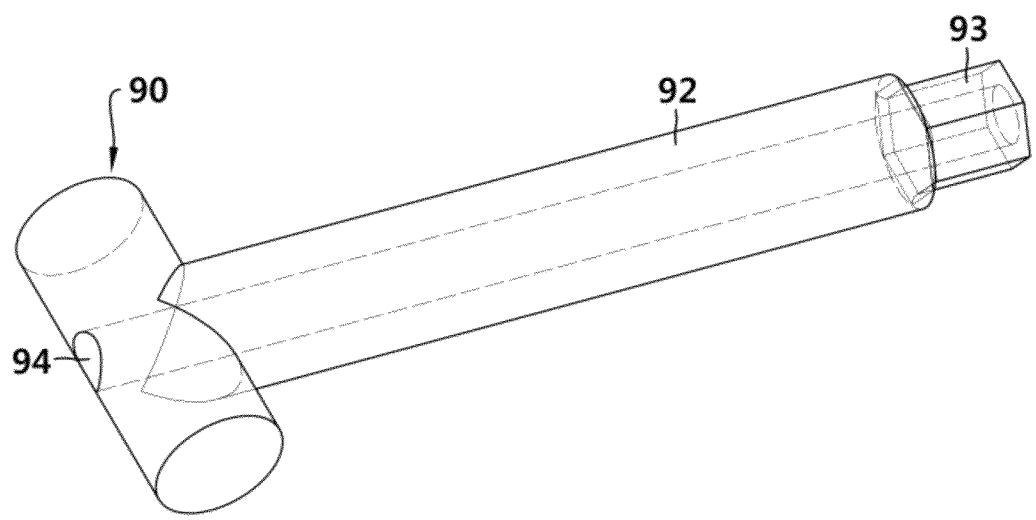
FIG. 5 is a perspective view illustrating a driver to be used in the pin assembly for operation of FIG. 4 according to the present invention.

FIG. 4 illustrates a pin assembly for operation having a screw type pin for operation according to another embodiment, in which a driver is connected to the pin for operation instead of the support. FIG. 5 illustrates the driver of FIG. 4 according to yet another embodiment.

Referring to FIG. 4a, the pin assembly 300 for operation may include a hollow pin 10g for operation having a plurality of side holes 30 defined on an outer surface and a thread 50 formed on a head 20, a hollow driver 90 for insertion into an opening formed on one side of the pin 10g for operation to transmit external force, and having a through-hole 94, an injector for insertion into the through-hole 94 of the driver 90, and a stylet 89 for insertion into a guide 88 of the injector 85.

A through-hole 40 is defined through the head 20 of the pin 10g for operation, and an inlet port 25 of the pin 10g for operation may have a hexagonal tubular form.

Further, FIG. 4b is a perspective view of a screw type pin assembly 300' for operation, which may include a hollow pin 10h for operation having a plurality of side holes 30 defined on an outer surface, and a through-hole 40 formed on a sharp head 20 at an end, a hollow driver 90 for insertion into an opening at one side of the pin 10h for operation to transmit external force, and having a through-hole 94, an injector 85 for insertion into the through-hole 94 of the driver 90, and a stylet 89 for insertion into a guide 88 of the injector 85.

The medication or bone cement, when fed from outside, is introduced through the guide 88 of the injector 85, past the interior of the driver 90 and arrives at the pin 10g for operation. The depth of insertion of the injector 85 is so adjusted to meet the side hole where medication injection is necessary, and medication is injected through a needle. If intramedullar intrusion is not efficiently made, the medication or bone cement can be easily pushed into the bone using the stylet 89 which is inserted into the guide 88.

A guide pin (not illustrated) or a reinforcement wire (not illustrated) may be arranged by being inserted through the through-hole 40 of the head 20 and the guide 88 of the driver 90 of the pin 10*g*, 10*h* for operation. In this case, a surgeon drives the guide pin into the bone via the skin, and exerts an external force on the support 60 or the driver 90 so that the pin 10*g*, 10*h* for operation is driven into the bone along the path of the guide pin (not illustrated). That is, the guide pin (not illustrated) guides the pin 10*g*, 10*h* for operation to be easily driven into the bone, and may not be removed but retained in an adequate size, in which case the guide pin (not illustrated) may reinforce the strength of the pin for operation as the reinforcement metal wire does.

Referring to the enlargement of FIG. 4*a* and to FIG. 5, he driver 90 has a cylindrical body 92 which has different diameters at both ends thereof. A through-hole 94 is defined through the center portion of the driver 90. An insertion part 93 having a hexagonal sectional shape is formed at the distal end of the body 92.

In the state in which the insertion part 93 of the driver 90 is fitted into the inlet port 25 of the pin 10*g* for operation and the head 20 of the pin 10*g* for operation is brought into direct contact with a portion of the bone to be treated, by applying external force to the driver 90, the pin 10*g* for operation can be driven into the bone. At this time, since force is transmitted through the driver 90 which is an integral element, the force can be concentrated rather than dispersed. Therefore, eventhough the thread 50 is formed on the head 20 of the pin 10*g* for operation, the pin 10*g* for operation can be easily driven into the bone.

The injector 85 is inserted into the through-hole 94 of the driver 90, and it is possible to adjust the depth of inserting the injector 85 for positioning at the through-hole of the pin for operation to allow introduction of the treatment agent to an intended site. The treatment agent may be pushed efficiently into the bone using the stylet 89, when there is resistance in the process of injecting the treatment agent.

The driver 90 is mainly used for a pin for operation which is formed with the thread 50. Thus, the pin 10*h* for operation shown in FIG. 1*h* can also be used together with the driver 50.

Figure 6:
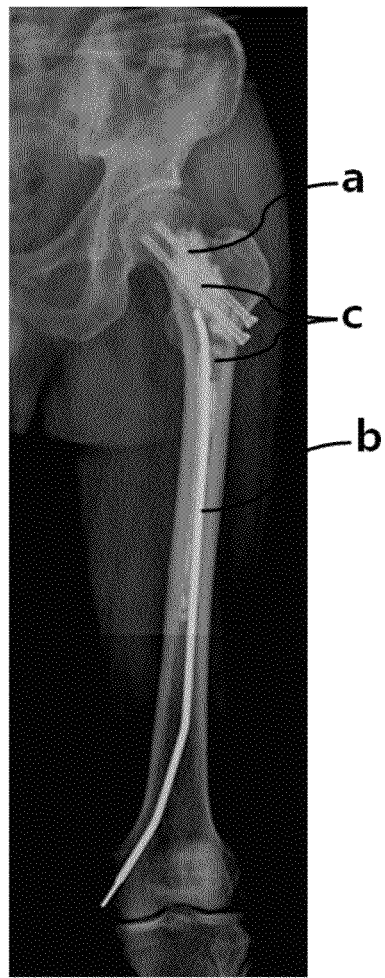
FIG. 6 is a radiograph obtained by penetrating X-rays through a bone having pins driven therein.

FIG. 6 is a radiograph obtained by penetrating X-rays through a bone having pins 10 driven therein. Referring to FIG. 6, a nail type pin 'b' for operation is completely inserted into the bone, a screw type pin 'a' for operation is inserted into the bone, and bone cement 'c' is injected into the bone.

Figure 7:
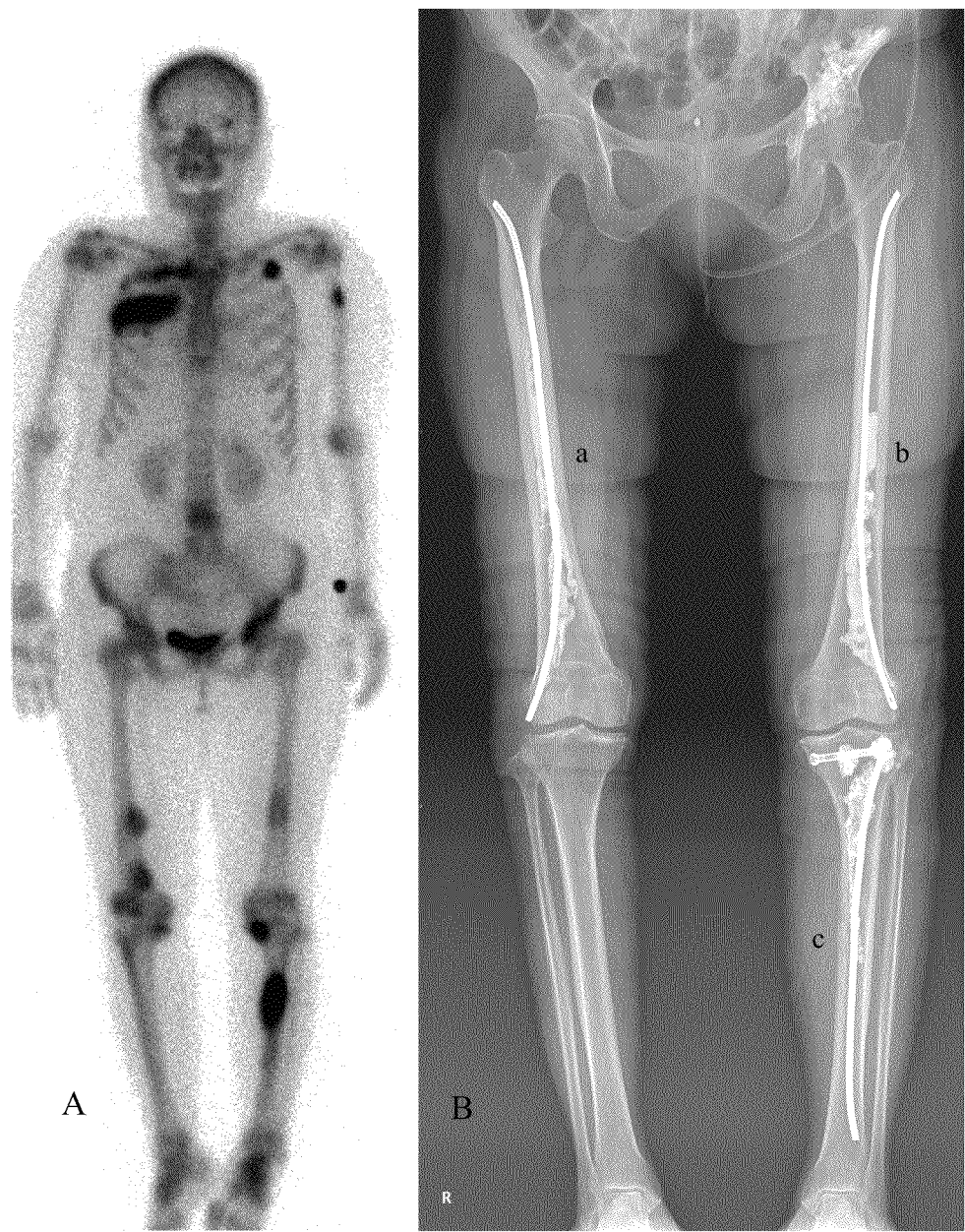
FIGS. 7a and 7b show a radiograph obtained by penetrating X-rays through the femur and tibia, the long bone, with the nail-type pin fixing the same, with the bone cement being simultaneously injected therein, according to an embodiment of the present invention.

FIG. 7 is a radiograph obtained by penetrating X-rays through a bone having nail type pins 10 driven into long bone of limb.

FIG. 7A is the bone scan image, showing multiple bone metastasis in bones including both femur and left tibia, before surgical operation, and FIG. 7B shows the nail type pin for operation being inserted into the long bone, and bone cement being injected (a, b, c) into the intramedullary bony lesion of metastatic bone cancer.

As explained above, an intramedullar nail type pin for operation is bendable itself before being driven into the bone, to suit the configuration of the long bones such as femur, humerus, or tibia. Further, the plurality of side holes may be formed on only an end of the nail type pin for operation, in which case the bone cement or medication can be limitedly focused to a lesion when the pin for operation is intramedullary inserted.

That is, the length of insertion of the long bone is measured in advance, and the pin for operation is driven intramedullary to arrange the side hole to the bone lesion. After that, medication or bone cement is injected into the bone through the hole defined in the pin for operation, and when sufficient amount of medication or bone cement is injected, the pin for operation is driven to the end so as to be completely placed within the medullar cavity before the bone cement hardens.

Figure 8:
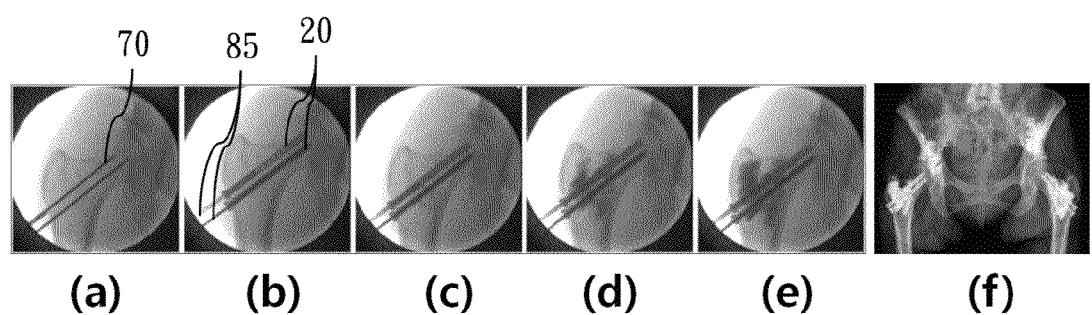
FIG. 8 is intra-operative fluoroscopy and post operative X-ray radiograph, showing the screw-type pin inserted into the femur neck, the short bone area, with the bone cement being simultaneously injected therein, according to an embodiment of the present invention.

FIG. 8 shows a screw type pin for operation 10*f* to 10*h* being inserted into femur neck in the process of surgical operation, according to an embodiment of the present invention.

Referring to FIG. 8, a screw type pin for operation is so configured that it is possible to adjust the position where the medication is injected, by inserting the injector into the tube of the pin for operation and arranging the same to meet the intended side hole. As explained above, minute adjustment is also possible, because medication or bone cement is injected into the bone, by inserting a separate injector into the driver and deep into the screw type pin for operation, and arranging the injector to the intended side hole of the pin for operation.

FIGS. 8(*a*) to 8(*e*) are intraoperative fluoroscopic radiographs, and FIG. 8(*g*) is postoperative X-ray radiograph. To be specific, FIG. 8(*a*) shows two guide pines 70 being inserted into the femur neck with metastatic bone cancer, and the screw type pin 20 for operation being inserted using the driver 90. After that, FIG. 8(*b*) shows a leading end of the injector 85 being positioned close to the lesion along the guide pins 70 driven into the central through-hole. FIGS. 8(*c*) and 8(*d*) show the guide pines 70 being removed, and medication or bone cement being injected through the guide 88 of the injector 85, and the medication or bone cement being charged into the bone starting from the side hole at the leading end of the injector 85 as the medication or bone cement within the injector 85 is pushed by the stylet 89.

After the injection is completed, and before medication or bone cement hardens, FIG. 8(*e*) shows the guide pins 70 being cut to meet the length of the pin 20 for operation, and pushed inward through the injector 85 for the purpose of bone reinforcement, and pushed by the stylet to be seated at the central through-hole of the pin 20 for operation. FIG. 8(*f*) shows the injector 85 and the stylet 89 being removed.

The pin for operation and the pin assembly for operation according to the present invention can be used only by defining a hole in the skin without the need of extensive incision of the skin or the muscle. Further, by injecting various medication or treatment agent in various ways through the internal passage and the side holes defined in the pin for operation, the pin for operation and the pin assembly for operation according to the present invention can be effectively used for bone metastasis, senile fracture, osteoporotic fracture, fracture nonunion, etc. As a consequence, since operation can be conveniently conducted within a short time without bleeding, advantages are conferred in that the general condition of a patient can be preserved and, when subsequent treatment is necessary, it can be immediately taken without loss of time.

Although preferred embodiments of the present invention have been described for illustrative purposes, those skilled in the art will appreciate that various modifications, additions and substitutions are possible, without departing from the scope and spirit of the invention as disclosed in the accompanying claims.

The invention claimed is:
1. A pin assembly for operation, comprising:
 a hollow pin for operation having a plurality of side holes defined through an outer surface thereof and a head which is closed or open due to the presence of a through-hole at the distal end thereof; a hollow support having a pin fastening part formed therein in the shape of a groove to fasten one end of the pin for operation, and being open at both ends thereof; and a hollow injector for insertion into an insertion hole formed in the support, wherein the hollow pin for operation is fastened to the pin fastening part of the support, and by applying external force to one end of the support, the hollow pin for operation is inserted into a bone curvature; and wherein a guide pin or a reinforcing metal wire is inserted through the hollow pin for operation and can be left an appropriate length to reinforce the strength of the hollow pin for operation inserted completely in the bone, and the hollow pin for operation, the guide pin and the reinforcing metal wire can be bent according to the bone shape.

2. A pin assembly for operation, comprising:

a hollow pin for operation having a plurality of side holes defined through an outer surface thereof, a head which is closed or open due to the presence of a through-hole at distal end thereof and a thread defined on the head;

a hollow support having a pin fastening part formed therein in the shape of a groove to fasten one end of the pin for operation, and being open at both ends thereof; and a hollow injector for insertion into an insertion hole formed in the support, wherein the hollow pin for operation is fastened to the pin fastening part of the support, and by applying external force to one end of the support, the hollow pin for operation is inserted into a bone curvature, and wherein by adjusting a position of a leading end of the hollow injector within the hollow pin, injection position of medication or bone cement injected into the bone is controlled, and wherein a guide pin or a reinforcing metal wire is inserted through the hollow pin for operation and can be left an appropriate length to reinforce the strength of the hollow pin for operation inserted completely in the bone.

3. The pin assembly according to claim 2, wherein the hollow pin for operation comprises:

a hollow conduit connected with one end to the head; and a cover for screw-coupling with the head, defining a predetermined space corresponding to a predetermined distance from an outer circumference of the conduit, and comprising a plurality of side holes defined therein, wherein an externally-injected material is stored in the predetermined space.

4. The pin assembly according to claim 2, further comprising a hollow driver comprising a through-hole formed therein, the hollow driver for insertion into an opening at one side of the hollow pin for operation.

5. The pin assembly according to claim 1, wherein the head of the hollow pin for operation is sharp, blunt or bent to one side.

6. The pin assembly according to claim 5, wherein the hollow pin for operation comprises side holes defined at an end of the head.

7. The pin assembly according to claim 5, wherein the hollow pin for operation comprise a fastening part at an end of the body.

8. The pin assembly according to claim 7, wherein the fastening part removably fastens the hollow pin for operation to the support by screw coupling.

9. The pin assembly according to claim 1, further comprising a stylet for insertion into the injector.

10. The pin assembly according to claim 2, wherein the injector comprises a handle with which it is possible to adjust the leading end of the injector to be positioned at the side holes of the hollow pin for operation in need of medication injection.

11. The pin assembly according to claim 1, further comprising a T-shaped impactor for insertion in between the insertion hole on the inner side of the support and the injector, the T-shaped impactor comprising a through-hole defined along the center.

12. The pin assembly according to claim 2, further comprising a stylet for insertion into the injector.

13. The pin assembly according to claim 1, wherein the hollow pin for operation is formed from stainless steel, titanium or an alloy using the same.

14. The pin assembly according to claim 1, wherein medication or bone cement is injected through the holes defined in the hollow pin for operation into the bone.

15. The pin assembly according to claim 14, wherein the medication is selected from the group consisting of alcohol, liquid nitrogen, anticancer medicine, bone regenerating material, and anti-resorptive agent.

* * * * *